United States Patent
Nakashima et al.

(10) Patent No.: US 10,583,036 B2
(45) Date of Patent: Mar. 10, 2020

(54) TOPICAL ADHESIVE SKIN PATCH

(71) Applicant: KANAE TECHNOS CO., LTD., Kanonji-shi, Kagawa (JP)

(72) Inventors: Shingo Nakashima, Kanonji (JP); Kazuhiro Yagyu, Kanonji (JP)

(73) Assignee: KANAE TECHNOS CO., LTD., Kanonji-shi (JP)

( * ) Notice: Subject to any disclaimer, the term of this patent is extended or adjusted under 35 U.S.C. 154(b) by 538 days.

(21) Appl. No.: 14/760,040

(22) PCT Filed: Dec. 13, 2013

(86) PCT No.: PCT/JP2013/007344
§ 371 (c)(1),
(2) Date: Jul. 9, 2015

(87) PCT Pub. No.: WO2014/112009
PCT Pub. Date: Jul. 24, 2014

(65) Prior Publication Data
US 2015/0335471 A1 Nov. 26, 2015

(30) Foreign Application Priority Data
Jan. 17, 2013 (JP) ................................ 2013-006125

(51) Int. Cl.
| | | |
|---|---|---|
| A61K 9/70 | (2006.01) | |
| A61K 9/10 | (2006.01) | |
| A61K 47/00 | (2006.01) | |
| A61F 7/02 | (2006.01) | |
| A61K 47/10 | (2017.01) | |
| A61K 47/22 | (2006.01) | |
| A61K 47/32 | (2006.01) | |
| A61K 47/34 | (2017.01) | |
| A61K 47/36 | (2006.01) | |
| A61K 47/38 | (2006.01) | |
| A61K 47/44 | (2017.01) | |

(52) U.S. Cl.
CPC .................. *A61F 7/02* (2013.01); *A61K 9/70* (2013.01); *A61K 47/10* (2013.01); *A61K 47/22* (2013.01); *A61K 47/32* (2013.01); *A61K 47/34* (2013.01); *A61K 47/36* (2013.01); *A61K 47/38* (2013.01); *A61K 47/44* (2013.01); *A61F 2007/0226* (2013.01)

(58) Field of Classification Search
None
See application file for complete search history.

(56) References Cited

U.S. PATENT DOCUMENTS

| | | | |
|---|---|---|---|
| 6,495,158 B1* | 12/2002 | Buseman | A61K 8/0208 424/401 |
| 2005/0208095 A1* | 9/2005 | Hunter | A61K 45/06 424/423 |
| 2005/0232983 A1* | 10/2005 | Sandage, Jr. | A61K 9/7061 424/449 |
| 2010/0130910 A1* | 5/2010 | Berenson | A61K 9/0009 604/20 |
| 2010/0239621 A1 | 9/2010 | Tsujihata | |
| 2012/0259018 A1* | 10/2012 | Bergman | A61K 9/06 514/570 |

FOREIGN PATENT DOCUMENTS

| | | |
|---|---|---|
| EP | 2210583 A1 | 7/2010 |
| JP | S56-154413 A | 11/1981 |
| JP | 2007-210941 A | 8/2007 |
| JP | 2009-108007 A | 5/2009 |
| JP | 2011-84542 A | 4/2011 |
| WO | 2009/057458 A1 | 5/2009 |

* cited by examiner

*Primary Examiner* — Abigail Vanhorn
(74) *Attorney, Agent, or Firm* — Metrolex IP Law Group, PLLC

(57) ABSTRACT

In a topical adhesive skin patch provided with a support and a base material layer laminated to one or both sides of the support, or in a topical adhesive skin patch intended to be used by placing only a gel sheet against the skin surface, the base material layer or gel sheet includes an oil-in-water type gel base containing at least water, oil, an emulsifier, and a water-absorbent polymer, such that prior to application to the skin surface, the base material layer or gel sheet is opaque due to emulsification of the base material layer or gel sheet, and subsequent to application to the skin surface, moisture contained in the base material layer or gel sheet gradually evaporates causing the opacity of the base material layer or gel sheet to decline over time, so that decline in opacity over time can be visually ascertained.

11 Claims, No Drawings

TOPICAL ADHESIVE SKIN PATCH

TECHNICAL FIELD

The present invention relates to a topical adhesive skin patch intended to be used by application to the skin surface.

BACKGROUND ART

Topical adhesive skin patches are intended to give cool sense or warm sense to the skin surface or percutaneously administer an active ingredient contained in the base material layer by being applied to the skin surface.

Such topical adhesive skin patches include those produced by laminating an emulsion-like, cream-like, ointment-like or gel-like base material layer on the back side of a sheet-like support formed of a nonwoven fabric, a resin sheet or a resin film, and those formed exclusively of a gel sheet produced by working a gel base into a sheet.

Recently, a base material having a transparent or translucent appearance while containing an oleophilic component, that does not lose the transparency even after evaporation of moisture from the composition, and is capable of keeping the transparency or translucency for a long time has been developed (for example, see Patent Document 1 below).

PRIOR ART DOCUMENT

Patent Document

Patent Document 1: Japanese Patent Laid-open Publication No. 2007-210941

SUMMARY OF THE INVENTION

Problems to be Solved by the Invention

By the way, topical adhesive skin patches of these types are generally so designed that a desired effect is exerted by being applied to the skin surface for a predetermined time ranging from approximately several minutes to several tens of minutes. Of course, there may be users who use the topical adhesive skin patch while measuring the precise time, however, it is the current state that many users stop using the patch after application according to their sensory decision. For this reason, one can discontinue the use in a short time before a lapse of a predetermined application time, and the other can continue application to the skin surface for a time longer than required.

When a user stops using the patch before a predetermined application time has lapsed, a sufficient effect is not obtained. On the other hand, when a patch is kept applied to the skin surface for a time longer than required, skin diseases such as a rash and eczema can occur on the skin surface.

The present invention was devised in light of these technical problems, and it is an object of the present invention to provide a novel topical adhesive skin patch by which the point in time to terminate application can be ascertained visually.

SOLUTIONS TO THE PROBLEMS

For solving the aforementioned technical problems, a first topical adhesive skin patch of the present invention includes a support, and a base material layer laminated to one or both sides of the support, and is intended to be used by placing an exposed surface of the base material layer against the skin surface, and the support is a resin mesh sheet or a porous resin sheet having a total light transmittance of greater than or equal to 80%, and the base material layer includes an oil-in-water type gel base containing at least water, oil, an emulsifier, and a water-absorbent polymer, such that prior to application to the skin surface, the base material layer is opaque due to emulsification of the base material layer, and subsequent to application to the skin surface, moisture contained in the base material layer gradually evaporates causing the opacity of the base material layer to decline over time, so that decline in opacity over time can be visually ascertained (hereinafter, referred to as the "first adhesive skin patch of the present invention").

In the present invention, the "total light transmittance of support" is a value measured in conformance with JIS K 7361 "Plastics—Test method for the total light transmittance of transparent materials." When a resin mesh sheet or a porous resin sheet having a total light transmittance of greater than or equal to 80% is used as the support, it becomes possible to visually ascertain the change in the state of the base material layer through the support. Examples of the support include those obtained by working a resin such as ionomer, polyvinyl chloride, polyvinylidene chloride, polyvinyl alcohol, polypropylene, polyester, polycarbonate, polystyrene, polyamide, or ethylene-polyvinyl alcohol copolymer into a mesh sheet or a sheet. As the support, those having a total light transmittance of greater than or equal to 80% (more preferably, greater than or equal to 90%) are preferably used, and the thickness of the support is not particularly limited.

On the other hand, when an oil-in-water type gel base containing at least water, oil, an emulsifier, and a water-absorbent polymer is used as the base material layer, the base material layer is opaque due to emulsification prior to application to the skin surface (during distribution to directly before use).

In the first adhesive skin patch of the present invention, since a resin mesh sheet or a porous resin sheet is used as the support, moisture contained in the base material layer that is warmed by the body temperature after application of the patch to the skin surface gradually evaporates into the atmospheric air through apertures of the resin mesh sheet or through-holes penetrating the front and back sides of the resin sheet. As the moisture in the base material layer decreases, the emulsion balance of the oil-in-water type gel base is disrupted, and the opacity of the base material layer declines over time, so that the light transmittance of the first adhesive skin patch of the present invention increases.

Defining the point in time when the skin surface becomes visible through the support and the base material layer as a result of decline of the opacity of the base material layer as the point in time to terminate application, the point in time to terminate application can be visually determined, and hence, the user will not terminate the use in a short time before a lapse of a predetermined application time, or will not continue application to the skin surface for a time longer than required.

The term "emulsification" used in the present invention includes not only the cloudy state but also turbid states in which red, blue, yellow and various other colors are added by components of the gel base constituting the base material. The term "visually ascertained" includes not only the meaning of visually identified directly by the user, but also visually identified indirectly by the user via a mirror, and visually identified by a person other than the user.

In the first adhesive skin patch of the present invention, since the required application time increases or decreases depending on, e.g., the nature of the active ingredient contained in the base material layer, it is preferred to control the speed of decline in opacity of the base material layer subsequent to application to the skin surface in accordance with the required application time. While the speed of decline in opacity of the base material layer can be controlled mainly by the formulation (kinds of water, oil, an emulsifier, and a water-absorbent polymer and the blending ratio among these components) of the oil-in-water type gel base which is to be the base material layer, or by the area occupied by the apertures or through-holes existing in the support (diameter×number), it is easier and preferred to control the speed of decline in opacity by the area occupied by the apertures or through-holes existing in the support rather than to control the speed of decline in opacity by the formulation of the gel base.

When the resin mesh sheet is used as the support, the mesh size of the resin mesh sheet is preferably selected within the range of 10 to 50 mesh (more preferably, within the range of 14 to 30 mesh) so as to prevent the gel base constituting the base material layer from oozing out to the front side of the support. On the other hand, when the porous resin sheet is used as the support, the diameter of the through-holes is preferably less than or equal to 2 mm (more preferably, within the range of 0.5 to 1.5 mm) so as to prevent the gel base constituting the base material layer from oozing out to the front side of the support. While the number of the through-holes can be determined appropriately depending on the required application time, and is not particularly limited, it is preferably within the range of $9 \times 10^4$ to $1 \times 10^6$ (more preferably, within the range of $3 \times 10^5$ to $8 \times 10^5$) per 1 m$^2$ of the support.

In the present invention, the "oil" means a hydrophobic substance that phase-separates from the water. Examples of the oil include hydrocarbons such as squalane, paraffin, and vaseline, fats and oils such as olive oil, almond oil, cacao oil, jojoba oil, macadamia nut oil, avocado oil, palm oil, castor oil, sunflower oil, evening primrose oil, and synthetic triglyceride, waxes such as beeswax, lanolin, carnauba wax, and candelilla wax, fatty acids such as stearic acid, oleic acid, myristic acid, palmitic acid, and behenic acid, higher alcohols such as cetanol, stearyl alcohol, behenyl alcohol, hexadecyl alcohol, octyl dodecyl alcohol, and cholesterol, synthetic esters such as IPM, glycerol triester, pentaerythritol tetraester, and cholesteryl ester, and silicone oils such as dimethylpolysiloxane, methylphenylpolysiloxane, and cyclomethicone. The blending percentage of the oil is preferably within the range of 10 to 50% by weight (more preferably, 20 to 40% by weight) to the total amount of the gel base constituting the base material layer.

In the present invention, the "emulsifier" means an amphiphilic molecule (surfactant) having a function of mixing water which is a polar substance with oil which is a nonpolar substance. Examples of the emulsifier include anionic surfactants such as higher fatty acid soap, alkyl sulfate ester salt, polyoxyethylene alkylether sulfate, acyl N-methyltaurine salt, alkylether phosphate ester salt, N-acylamino acid salt, cationic surfactants such as alkyltrimethylammonium chloride, dialkyldimethylammonium chloride, and benzalkonium chloride, amphoteric surfactants such as alkyl dimethylamino acetic acid betaine, alkylamide dimethylamino acetic acid betaine, and 2-alkyl-N-carboxy-N-hydroxyimidazolium betaine, and nonionic surfactants such as glyceryl monostearate, sorbitan monostearate, POE alkyl ether, POE-POP block copolymer, POE hardened castor oil ester, polyoxyethylene sorbitan oleate, inulin lauryl carbamate, and acrylates/alkyl acrylate cross polymer. Preferably, the HLB of the emulsifier is within the range of 7 to 18 (more preferably, 8 to 16). The blending percentage of the emulsifier is preferably within the range of 0.2 to 3.0% by weight (more preferably, 0.4 to 2.0% by weight) to the total amount of the gel base constituting the base material layer.

Further, in the present invention, the "water-absorbent polymer" is a general term for polymers having excellent water absorbency and capable of retaining a large amount of water (for example, water of 100 times to 1000 times or more the self weight), and means those having the property of capturing a large number of water molecules in a network structure formed by the polymer to make them into a gel form. Examples of the water-absorbent polymer include polyvinyl alcohol, polyvinyl pyrrolidone, polyacrylic acid and salts thereof, synthetic polymeric hydrophilic polymers such as maleic anhydride copolymer, natural hydrophilic polymers such as dextran, pullulan, gelatin, agarose, carrageenan, locust bean gum, xanthan gum, mannan, gellan gum, sodium alginate, pectin, and guar gum, and semi-synthetic compounds such as methyl cellulose, ethyl cellulose, carboxymethyl cellulose, hydroxyethyl cellulose, and hydroxypropylmethyl cellulose. The blending percentage of the water-absorbent polymer is preferably within the range of 1 to 12% by weight (more preferably, 2 to 10% by weight) to the total amount of the gel base constituting the base material layer.

In the first adhesive skin patch of the present invention, a preferred aspect is such that the opacity of the base material layer laminated to the support is greater than or equal to 90% prior to application to the skin surface, and declines to less than or equal to 65% over time subsequent to application to the skin surface.

In the present invention, the "opacity (haze)" is a value measured in conformance with JIS K 7136 "Plastics—Determination of haze for transparent materials." In the first adhesive skin patch of the present invention, the opacity is the opacity of the base material layer laminated to the support, namely the opacity of the first adhesive skin patch of the present invention itself.

When the opacity is greater than or equal to 90%, the skin surface cannot be visually recognized through the support and the base material. On the other hand, when the opacity declines to less than or equal to 65% subsequent to application to the skin surface, the skin surface becomes apparently visible through the support and the base material layer.

While the opacity can be controlled mainly by the formulation of the gel base or the lamination thickness of the base material layer, it is easier and preferred to control the opacity by the lamination thickness of the base material layer rather than to control the opacity by the formulation of the gel base in the first adhesive skin patch of the present invention.

In the first adhesive skin patch of the present invention, a preferred aspect is such that the total light transmittance of the light flux having transmitted through the support and the base material layer is less than or equal to 60% prior to application to the skin surface, and increases to greater than or equal to 80% over time subsequent to application to the skin surface.

The "total light transmittance of a light flux having transmitted through the support and the base material layer" is a value measured in conformance with JIS K 7361 "Plastics—Test method for the total light transmittance of transparent materials" likewise the foregoing "total light transmittance of support." In the first adhesive skin patch of the present invention, the "total light transmittance of a light flux having transmitted through the support and the base material layer" is the total light transmittance of the first adhesive skin patch of the present invention itself.

When the total light transmittance of the first adhesive skin patch of the present invention itself is less than or equal to 60%, the skin surface cannot be visually recognized through the support and the base material. On the other hand, when the total light transmittance of the first adhesive skin patch of the present invention itself increases to greater than or equal to 80% subsequent to application to the skin surface, the skin surface becomes apparently visible through the support and the base material layer.

While the total light transmittance can be controlled by the formulation of the gel base or the lamination thickness of the base material layer, it is easier and preferred to control the total light transmittance by the lamination thickness of the base material layer rather than to control the total light transmittance by the formulation of the gel base in the first adhesive skin patch of the present invention.

In the first adhesive skin patch of the present invention, a preferred aspect is such that the blending ratio between water and oil in the base material layer prior to application to the skin surface is 1:0.2 to 1:1.5.

When the blending proportion of oil in the base material layer prior to application to the skin surface is large, the time required for the skin surface to be visible through subsequent to application to the skin surface tends to be short. Therefore, when the required application time is short, the blending proportion of the oil in the base material layer can be increased, and when the required application time is long, the blending proportion of the water in the base material layer can be increased.

Many of general topical adhesive skin patches are so designed that a desired effect is obtained by an application time of about 10 to 30 minutes, and for making the skin surface to be visible through in such an application time, the blending ratio between water and oil in the base material layer prior to application to the skin surface can be set within the range of 1:0.2 to 1:1.5.

In the first adhesive skin patch of the present invention, a preferred aspect is such that the emulsifier is a non-ionic surfactant.

Since the first adhesive skin patch of the present invention is intended to be used by application to the skin surface, a non-ionic surfactant that is less irritant to the skin compared with an ionic surfactant is preferably used. Among others, inulin lauryl carbamate capable of drawing a lot of oil into water to form an oil-in-water type emulsion, in which the ratio between oil and water can be adjusted over a wide range, is preferably used as the emulsifier.

In the first adhesive skin patch of the present invention, a preferred aspect is such that the exposed surface of the base material layer is covered with a non-breathable protective sheet.

Since the first adhesive skin patch of the present invention is so designed that the base material layer is opaque prior to application to the skin surface, and moisture contained in the base material evaporates to make the skin surface visible through the support and the base material subsequent to application to the skin surface, it is undesired that the moisture evaporates from the exposed surface of the base material layer during distribution and storage of the first adhesive skin patch of the present invention. As a countermeasure for this, for example, the first adhesive skin patch of the present invention may be enclosed in a non-breathable bag member, and subjected to distribution or storage in the condition that the exposed surface of the base material layer is applied to the inner surface of the bag member. However, when the first adhesive skin patch of the present invention adhered to the inner surface of the bag member is detached and taken out of the bag member, the base material layer can partly remain in the bag member or the base material can tear.

Therefore, in the first adhesive skin patch of the present invention, it is preferred to cover the exposed surface of the base material layer with a non-breathable protective sheet such as a resin film or a resin sheet, thereby preventing moisture from evaporating from the exposed surface of the base material layer during distribution and storage, and making a user use the adhesive skin patch after removal of the protective sheet.

A second adhesive skin patch of the present invention is a topical adhesive skin patch intended to be used by placing only a gel sheet against the skin surface, and the gel sheet is obtained by working an oil-in-water type gel base containing at least water, oil, an emulsifier, and a water-absorbent polymer into a sheet, such that prior to application to the skin surface, the gel sheet is opaque due to emulsification of the gel sheet, and subsequent to application to the skin surface, moisture contained in the gel sheet gradually evaporates casing the opacity of the gel sheet to decline over time (hereinafter, referred to as the "second adhesive skin patch of the present invention").

The second adhesive skin patch of the present invention is intended to be used by placing only a gel sheet against the skin surface, and differs from the first adhesive skin patch of the present invention in that it is not used in the condition that the support is laminated. The gel base constituting the gel sheet is similar to the gel base constituting the base material layer in the first adhesive skin patch of the present invention. That is, similarly to the first adhesive skin patch of the present invention, the second adhesive skin patch of the present invention is so designed that, prior to application to the skin surface, the gel sheet is opaque due to emulsification of the gel sheet, and subsequent to application to the skin surface, moisture contained in the gel sheet gradually evaporates casing the opacity of the gel sheet to decline over time, so that decline in opacity over time can be visually ascertained.

The blending percentage of the oil in the gel sheet is preferably within the range of 10 to 50% by weight (more preferably, 20 to 40% by weight) to the total amount of the gel base constituting the gel sheet.

The blending percentage of the emulsifier in the gel sheet is preferably within the range of 0.2 to 3.0% by weight (more preferably, 0.4 to 2.0% by weight) to the total amount of the gel base constituting the gel sheet.

The blending percentage of the water-absorbent polymer in the gel sheet is preferably within the range of 1 to 12% by weight (more preferably, 2 to 10% by weight) to the total amount of the gel base constituting the gel sheet.

In the second adhesive skin patch of the present invention, a preferred aspect is such that the gel strength of the gel sheet measured in the following test ranges from 3 to 20 N/50 mm.
<Test>
The gel sheet of 50 mm wide and long is gripped at a chuck distance of 200 mm, the tensile stress is measured by stretching the gel sheet in the longitudinal direction at a tensile speed of 300 mm per minute, and the maximum tensile stress at which the gel sheet ruptures is determined as the gel strength.

It has been proved that the gel strength of the gel sheet increases with the thickness of the gel sheet. The thickness of the gel sheet is preferably in the range of 0.3 to 5 mm (more preferably, 0.5 to 2 mm). In the second adhesive skin patch of the present invention, it is preferred to use a highly shape-retentive natural hydrophilic polymer such as dextran, pullulan, gelatin, agarose, carrageenan, locust bean gum, xanthan gum, mannan, gellan gum, sodium alginate, pectin, or guar gum as the water-absorbent polymer.

In the second adhesive skin patch of the present invention, a preferred aspect is such that the opacity when the gel sheet is viewed from the front side to the back side is greater than or equal to 90% prior to application to the skin surface, and declines over time to less than or equal to 65% subsequent to application to the skin surface.

In the second adhesive skin patch of the present invention, a preferred aspect is such that the total light transmittance of the light flux having transmitted from the front side to the back side of the gel sheet is less than or equal to 60% prior to application to the skin surface, and increases over time to less than or equal to 80% subsequent to application to the skin surface.

In the second adhesive skin patch of the present invention, a preferred aspect is such that the blending ratio between water and oil in the gel sheet prior to application to the skin surface is 1:0.2 to 1:1.5.

In the second adhesive skin patch of the present invention, a preferred aspect is such that the emulsifier is a non-ionic surfactant.

In the second adhesive skin patch of the present invention, a preferred aspect is such that the front and back sides of the gel sheet are covered with a non-breathable protective sheet, and the protective sheet is removed before use.

In the second adhesive skin patch of the present invention, a preferred aspect is such that the gel sheet is enclosed in a non-breathable bag member, and the bag member is opened and the gel sheet is taken out before use.

EFFECTS OF THE INVENTION

According to the present invention, it is possible to visually ascertain the point in time to terminate application.

EMBODIMENTS OF THE INVENTION

Hereinafter, embodiments of the present invention will be described by way of examples, however, it is to be noted that the present invention will not be limited to these examples.

EXAMPLES 1 TO 6

—First Adhesive Skin Patch of the Present Invention—

<Support>

As a support, a resin mesh sheet (300×1000 mm) of polyethylene terephthalate resin (PET) having a mesh size of 22 mesh and a thickness of 114 μm was used.

<Base Material Layer>

As a base material constituting a base material layer, an oil-in-water type gel base having the components and the blending ratio shown in Table 1 below was used. The gel base was stirred uniformly with a mixer, and then laminated to the entire surface of one side of the support into a uniform thickness (400 g/m$^2$) to give the base material layer, and it was in an emulsified state prior to application to the skin surface.

TABLE 1

| | | Example | | | | | |
|---|---|---|---|---|---|---|---|
| Component (parts by weight) | | 1 | 2 | 3 | 4 | 5 | 6 |
| Emulsifier | Inulin lauryl carbamate | 0.8 | 0.8 | 0.8 | | | |
| | Acrylates/ C10-30 alkyl acrylate cross polymer | | | | 0.8 | | |
| | Polyoxyethylene hardened castor oil | | | | | 2.0 | |
| | Polysorbate | | | | | | 2.0 |
| Water-absorbent polymer | Sodium polyacrylate | | | | 4.5 | | |
| | Polyacrylic acid | | | | | 1.6 | |
| | Carboxymethyl cellulose | | | | | | 3.0 |
| Oil | Olive oil | 40.0 | | | | | |
| | Triethylhexanoine | | 40.0 | | 40.0 | 40.0 | 40.0 |
| | Jojoba oil | | | 40.0 | | | |
| | Tocopherol acetate | | | 0.3 | | | |
| Water Additive | Purified water | | | 34.16 | | 33.13 | |
| | Glycerin | | | 15.0 | | | |
| | Magnesium aluminometa silicate | | | 0.12 | | | |
| | Tartaric acid | | | 0.2 | | | |
| | EDTA-2Na | | | 0.15 | | | |

<Measurement of Opacity>

For the first adhesive skin patches of the present invention according to Examples 1 to 6, the opacity was measured prior to application to the skin surface and subsequent to application to the skin surface when the skin surface became visible through the support and the base material layer. The opacity was determined by measuring the state of the base material layer seen through the support. The opacity was measured in conformance with JIS K 7136 by using NDH5000SP available from NIPPON DENSHOKU INDUSTRIES Co., LTD.

<Measurement of Total Light Transmittance>

For the first adhesive skin patches of the present invention according to Examples 1 to 6, the total light transmittance was measured prior to application to the skin surface and subsequent to application to the skin surface when the skin surface became visible through the support and the base material layer. The total light transmittance was determined by measuring the transmittance when the light flux transmitted through the support and the base material. The opacity was measured in conformance with JIS K 7361 by using NDH5000SP available from NIPPON DENSHOKU INDUSTRIES Co., LTD.

The measurement results of the opacity and the total light transmittance are shown in Table 2 below.

TABLE 2

| | | Example | | | | | |
|---|---|---|---|---|---|---|---|
| | | 1 | 2 | 3 | 4 | 5 | 6 |
| Opacity (%) | Prior to application | 99.26 | 99.74 | 99.56 | 99.36 | 99.03 | 99.23 |
| | Subsequent to application | 60.05 | 61.15 | 61.04 | 60.12 | 58.88 | 60.01 |
| Total light transmittance (%) | Prior to application | 59.02 | 58.76 | 58.87 | 58.92 | 58.66 | 58.98 |
| | Subsequent to application | 87.69 | 86.38 | 86.58 | 86.77 | 86.48 | 87.60 |

The results shown in Table 2 revealed that in any of the first adhesive skin patches of the present invention according to Examples 1 to 6, the opacity was greater than or equal to 90% and the total light transmittance was less than or equal to 60% prior to application to the skin surface.

It was also revealed that in any of the first adhesive skin patches of the present invention according to Examples 1 to 6, the opacity declined over time to less than or equal to 65%, and the total light transmittance increased to greater than or equal to 80% subsequent to application to the skin surface.

It was revealed that the first adhesive skin patch of the present invention that was opaque due to emulsification of the base material prior to application to the skin surface changed so that the skin color of the skin surface could be seen through the support and the base material layer by the change in opacity or total light transmittance subsequent to the application to the skin surface.

EXAMPLES 7 TO 9

—First Adhesive Skin Patch of the Present Invention—
<Support>

As a support, a porous resin sheet (300×1000 mm) of polyethylene terephthalate resin (PET) having a thickness of 110 μm was used. The resin sheet has a plurality (749×10$^3$/m$^2$) of through-holes (φ:1 mm) penetrating the front and back sides, arranged at regular intervals.

<Base Material Layer>

As the base material that forms the base material layer, an oil-in-water type gel base having the components and the blending ratio shown in Table 3 below was used. The gel base was stirred uniformly with a mixer, and then laminated to the entire surface of one side of the support into a uniform thickness (400 g/m$^2$) to give the base material layer, and it was in an emulsified state prior to application to the skin surface.

TABLE 3

| Component (parts by weight) | | Example 7 | Example 8 | Example 9 |
|---|---|---|---|---|
| Emulsifier | Inulin lauryl carbamate | 0.2 | 0.8 | 1.0 |
| Water-absorbent polymer | Sodium polyacrylate | 5.5 | 4.5 | 3.0 |
| | Polyacrylic acid | 1.6 | 1.6 | |
| | Carboxymethyl cellulose | 3.5 | 3.0 | 1.5 |
| Oil | Olive oil | 10.0 | | |
| | Triethylhexanoine | | 40.0 | |
| | Jojoba oil | | | 50.0 |
| | Tocopherol acetate | | 0.3 | |
| Water | Purified water | 50.33 | 34.16 | 33.63 |
| Additive | EDTA-2Na | 0.1 | 0.15 | 0.15 |
| | Tartaric acid | | 0.2 | |
| | Methylparaben | | 0.12 | |
| | Glycine Al | | 0.05 | |
| | Magnesium aluminometasilicate | 0.15 | 0.12 | 0.1 |
| | Glycerin | 28.0 | 15.0 | 10.0 |

For the first adhesive skin patches of the present invention according to Examples 7 to 9, the opacity and the total light transmittance were measured in a similar manner to Examples 1 to 6, and it was revealed that in any of these, the opacity was greater than or equal to 90% and the total light transmittance was less than or equal to 60% prior to application to the skin surface. It was also revealed that in any of these, the opacity declined over time to less than or equal to 65%, and the total light transmittance increased to greater than or equal to 80% subsequent to application to the skin surface.

For the first adhesive skin patches of the present invention according to Examples 7 to 9, the times required for the opacity to decline to less than or equal to 65% and for the total light transmittance to increase to greater than or equal to 80% subsequent to the application to the skin surface are shown in Table 4 below.

TABLE 4

| | Example 7 | Example 8 | Example 9 |
|---|---|---|---|
| Water:Oil (weight ratio) | 1:0.2 | 1:1.2 | 1:1.5 |
| Required time (min.) | 29.5 | 15.0 | 10.5 |

The results shown in Table 4 revealed that in the first adhesive skin patch of the present invention, the time required for the skin surface to become visible through subsequent to application to the skin surface can be controlled by adjusting the ratio between water and oil in the gel base constituting the base material layer. More specifically, it was revealed that the time required for the skin surface to become visible through subsequent to application to the skin surface tends to decrease as the amount of oil relative to the amount of water contained in the gel base increases.

This revealed that the blending ratio between water and oil in the gel base constituting the base material layer can be selected within the range of 1:0.2 to 1:1.15 to make the time required for the skin surface to become visible through subsequent to application to the skin surface fall within the range of 10 to 30 minutes when the base material layer is laminated to the support used in the present example.

It was also revealed that also by increasing or decreasing the area occupied by the through-holes provided in the support, the time required for the skin surface to become visible through subsequent to application to the skin surface can be controlled.

As various additives including EDTA-2Na serving as a chelator, tartaric acid serving as a pH modifier, methylparaben serving as an antiseptic, glycine Al and magnesium aluminometasilicate serving as a gel strength modifier, and glycerin serving as a humectant are blended in the gel base constituting the base material layer in Examples 1 to 9, the first adhesive skin patch of the present invention can contain these various additives as necessary besides the water, the oil, the emulsifier, and the water-absorbent polymer. It is also revealed that even when these additives are not blended, the base material layer is emulsified prior to application to the skin surface, and the opacity declines over time and the total light transmittance increases subsequent to application to the skin surface.

While the base material layer is laminated to one side of the support in Examples 1 to 9, it is reveled that even when the base material layer is laminated to both sides of the support, the base material layer is emulsified prior to application to the skin surface, and the opacity declines over time and the total light transmittance increases subsequent to application to the skin surface.

EXAMPLE 10

—Second Adhesive Skin Patch of Present Invention—
<Gel Sheet>

A gel sheet having a thickness of 1 mm was prepared by using an oil-in-water type gel base having the components and the blending ratio shown in Table 5 below. The gel sheet was emulsified prior to application to the skin surface.

TABLE 5

| Component (parts by weight) | | Example 10 |
|---|---|---|
| Emulsifier | Polyoxyethylene hardened castor oil | 1.50 |
| Water-absorbent polymer | Xanthan gum | 0.38 |
| | Locust bean gum | 0.38 |
| | Agarose | 1.50 |
| Oil | Olive oil | 30.00 |
| Water | Purified water | 45.64 |
| Additive | EDTA-2Na | 0.10 |
| | 1-3-Butylene glycol | 5.00 |
| | Glycerin | 10.00 |
| | Phenoxyethanol | 0.50 |
| | Dipropylene glycol | 2.00 |
| | Pentylene glycol | 3.00 |

For the gel sheet, the opacity and the total light transmittance were measured in a similar manner to Examples 1 to 9, and the opacity was greater than or equal to 90%, and the total light transmittance was less than or equal to 60% prior to application to the skin surface. It was also reveled that the opacity declined over time to less than or equal to 65%, and the total light transmittance increased to greater than or equal to 80% subsequent to application to the skin surface.

As various additives including EDTA-2Na serving as a chelator, phenoxyethanol, dipropylene glycol, and pentylene glycol serving as an antiseptic, and 1-3-butylene glycol and glycerin serving as a humectant are blended in the gel base constituting the gel sheet in Example 10, the second adhesive skin patch of the present invention can contain these various additives as necessary besides the water, the oil, the emulsifier, and the water-absorbent polymer. It is also reveled that even when these additives are not blended, the gel sheet is emulsified prior to application to the skin surface, and the opacity declines over time and the total light transmittance increases subsequent to application to the skin surface.

<Measurement of Gel Strength>

For the gel sheet which is the second adhesive skin patch of the present invention according to Example 10, the gel strength was measured and the results are shown in Table 6 below. The gel strength was determined by gripping the gel sheet cut into a band shape of 50 mm wide and long at a chuck distance of 200 mm by Autograph AGS-N-100N available from Shimadzu Corporation, stretching the gel sheet in the longitudinal direction at a tensile speed of 300 mm per minute, measuring the maximum tensile stress at which the gel sheet ruptured a total of three times, and averaging the measurements.

TABLE 6

| Number of times of measurement (n) | Gel strength (N/50 mm) |
|---|---|
| n: 1 | 6.48 |
| n: 2 | 7.27 |
| n: 3 | 4.98 |
| Average value | 6.24 |

It was reveled that in the second adhesive skin patch of the present invention, the gel strength of the gel sheet can be adjusted mainly by adjusting the proportion or the kind of the water-absorbent polymer, or the blending proportion of water in the gel base constituting the gel sheet. It was also revealed that the gel strength tends to increase as the thickness of the gel sheet increases. It was also reveled that excellent shape retainability is obtained when the gel strength of the gel sheet falls within the range of 3 to 20 N/50 mm.

The present invention can be practiced in other various forms without departing from the spirit and main features thereof. Therefore, the foregoing examples are merely exemplification in all aspects, and should not be interpreted limitedly. The scope of the present invention is defined by claims, and will be never restricted by the description. Further, any modifications and changes belonging to the equivalents of claims are included in the scope of the present invention.

INDUSTRIAL APPLICABILITY

Both of the first adhesive skin patch of the present invention and the second adhesive skin patch of the present invention are preferably used as a topical adhesive skin patch intended to be used by application to the skin surface.

The invention claimed is:
1. A topical adhesive skin patch comprising a support, and a base material layer laminated to one or both sides of the support, intended to be used by placing an exposed surface of the base material layer against the skin surface, wherein
   the support is a resin mesh sheet or a porous resin sheet having a plurality of through-holes penetrating from a front side and a back side thereof, the support having a total light transmittance of greater than or equal to 80%, and
   the base material layer includes an oil-in-water type gel base containing at least water, oil, an emulsifier, and a water-absorbent polymer,
   blending percentages of the oil, the emulsifier, and the water-absorbent polymer in the gel base are set within a range of 10 to 50% by weight of the oil to the total amount of the gel base, within a range of 0.2 to 3.0% by weight of the emulsifier to the total amount of the gel base, and within a range of 1 to 12% by weight of the water-absorbent polymer to the total amount of the gel base,
   a blending ratio between the water and the oil in the base material layer prior to application to the skin surface is 1:0.2 to 1:1.2, and
   a mesh size of the resin mesh sheet is set within a range of 10 to 50 mesh or a number of the through-holes, having a diameter of 0.5 to 1.5 mm, of the porous resin sheet is set within a range of $9 \times 10^4$ to $1 \times 10^6$ per 1 $m^2$ such that the base material layer comprises opaque characteristics in which
   prior to application to the skin surface, the base material layer is opaque due to emulsification of the base material layer, and
   subsequent to application to the skin surface, moisture contained in the base material layer gradually evaporates causing the opacity to decline over time, wherein the opacity of the base material layer laminated to the support is greater than or equal to 90% prior to application to the skin surface, and the opacity of the base material layer declines over time to less than or equal to 65% subsequent to application to the skin surface, so that the decline in opacity of the base material layer over time can be visually ascertained by the skin surface becoming visible through the support.

2. The topical adhesive skin patch according to claim 1, wherein
the total light transmittance of a light flux having transmitted through the support and the base material layer is
less than or equal to 60% prior to application to the skin surface, and
increases to greater than or equal to 80% over time subsequent to application to the skin surface.

3. The topical adhesive skin patch according to claim 1, wherein
the emulsifier is a non-ionic surfactant.

4. The topical adhesive skin patch according to claim 1, wherein
the exposed surface of the base material layer is covered with a non-breathable protective sheet.

5. The topical adhesive skin patch according to claim 1, wherein the mesh size of the resin mesh sheet is set within a range of 14 to 30 mesh.

6. The topical adhesive skin patch according to claim 1, wherein the number of through-holes is within a range of $3\times10^5$ to $8\times10^5$ per 1 $m^2$.

7. The topical adhesive skin patch according to claim 1, wherein the blending percentage of the oil is within a range of 20 to 40% by weight to the total amount of the gel base.

8. The topical adhesive skin patch according to claim 1, wherein the blending percentage of the emulsifier is within a range of 0.4 to 2.0% by weight to the total amount of the gel base.

9. The topical adhesive skin patch according to claim 1, wherein the blending percentage of the water-absorbent polymer is within a range of 2 to 10% by weight to the total amount of the gel base.

10. The topical adhesive skin patch according to claim 1, wherein the blending ratio between the water and the oil in the base material layer prior to application to the skin surface is 1:0.66 to 1:1.2.

11. The topical adhesive skin patch according to claim 1, wherein the blending ratio between the water and the oil in the base material layer prior to application to the skin surface is 1:0.2 to 1:0.66.

* * * * *